US011925880B2

(12) United States Patent
Baxter et al.

(10) Patent No.: US 11,925,880 B2
(45) Date of Patent: Mar. 12, 2024

(54) SEPARATION OF COMPOUNDS

(71) Applicant: Sustainable Energy Solutions, Inc., Provo, UT (US)

(72) Inventors: Larry Baxter, Orem, UT (US); Chris Hoeger, Provo, UT (US); Stephanie Burt, Provo, UT (US); Kyler Stitt, Lindon, UT (US); Aaron Sayre, Spanish Fork, UT (US); Skyler Chamberlain, Provo, UT (US)

(73) Assignee: Sustainable Energy Solutions, Inc., Orem, UT (US)

( * ) Notice: Subject to any disclaimer, the term of this patent is extended or adjusted under 35 U.S.C. 154(b) by 420 days.

(21) Appl. No.: 16/133,339

(22) Filed: Sep. 17, 2018

(65) Prior Publication Data

US 2020/0086238 A1    Mar. 19, 2020

(51) Int. Cl.
*B01D 17/00* (2006.01)
*B01D 17/02* (2006.01)
*B01D 21/00* (2006.01)
*C07C 7/00* (2006.01)

(52) U.S. Cl.
CPC ......... *B01D 17/10* (2013.01); *B01D 17/0214* (2013.01); *B01D 21/009* (2013.01); *C07C 7/00* (2013.01)

(58) Field of Classification Search
None
See application file for complete search history.

(56) References Cited

U.S. PATENT DOCUMENTS

| | | | | |
|---|---|---|---|---|
| 7,862,332 B2* | 1/2011 | Schwab | ................ | F27B 7/20 |
| | | | | 432/15 |
| 8,945,350 B2* | 2/2015 | Bratina | ............ | C10M 175/0033 |
| | | | | 34/247 |
| 2012/0024687 A1* | 2/2012 | Bratina | ................ | B01D 1/223 |
| | | | | 203/22 |
| 2012/0027662 A1* | 2/2012 | Bratina | ................ | C01B 32/40 |
| | | | | 423/418.2 |
| 2014/0101986 A1* | 4/2014 | Botero | ................ | B01J 13/00 |
| | | | | 44/280 |
| 2018/0170783 A1* | 6/2018 | Baxter | ................ | C02F 11/125 |
| 2020/0086238 A1* | 3/2020 | Baxter | ................ | C07C 7/00 |

OTHER PUBLICATIONS

Sustainable Energy Solutions, Skid-Scale Cryogenic Carbon Capture, Larry Baxter, 26 pages, Aug. 2014. (Year: 2014).*

* cited by examiner

*Primary Examiner* — Robert J Popovics
(74) *Attorney, Agent, or Firm* — Cook Alex Ltd.

(57) ABSTRACT

A method for separating liquids is disclosed. A feed stream is passed into a separator. The feed stream comprising an organic compound, carbon dioxide, and oxides selected from the group consisting of sulfur oxides, nitrogen oxides, ozone and combinations thereof. A portion an organic-rich stream is separated from a portion of an inorganic-rich stream through separation by gravity. The organic-rich stream contains a portion of the organic compound and a first portion of the carbon dioxide. The inorganic-rich stream contains a portion of the oxides and a second portion of the carbon dioxide.

9 Claims, 4 Drawing Sheets

SEPARATION OF COMPOUNDS

GOVERNMENT INTEREST STATEMENT

This invention was made with government support under DE-FE0028697 awarded by the Department of Energy. The government has certain rights in the invention.

TECHNICAL FIELD

The devices and processes described herein relate generally to separation of organic and inorganic phases. More particularly, the devices and processes described herein relate to systems and methods for separating sulfur and nitrogen oxides from organic compounds.

BACKGROUND

Flue gases are often treated with organic solvents to remove carbon dioxide from the flue gas. Flue gas often contains acid gases other than just carbon dioxide, such as sulfur oxides, nitrogen oxides, and ozone, which are also removed. However, separating these oxides from each other and from carbon dioxide can be challenging. While typical distillation can be utilized, this can be both energy and capital intensive.

SUMMARY

In a first aspect, the disclosure provides a method for separating compounds. A feed stream is passed into a separator. The feed stream consists of an organic compound, carbon dioxide, and oxides selected from the group consisting of sulfur oxides, nitrogen oxides, ozone, and combinations thereof. A portion of an organic-rich stream is separated by gravity from a portion of an inorganic-rich stream. The organic-rich stream contains a portion of the organic compound and a first portion of the carbon dioxide. The inorganic-rich stream contains a portion of the oxides and a second portion of the carbon dioxide.

In a second aspect, the separator contains an auger, a portion of the carbon dioxide and the oxides are solids, and the auger is heated to melt a portion of those solids.

Further aspects and embodiments are provided in the foregoing drawings, detailed description and claims.

BRIEF DESCRIPTION OF THE DRAWINGS

The following drawings are provided to illustrate certain embodiments described herein. The drawings are merely illustrative, and are not intended to limit the scope of claimed inventions and are not intended to show every potential feature or embodiment of the claimed inventions. The drawings are not necessarily drawn to scale; in some instances, certain elements of the drawing may be enlarged with respect to other elements of the drawing for purposes of illustration.

DETAILED DESCRIPTION

Figure 1A:
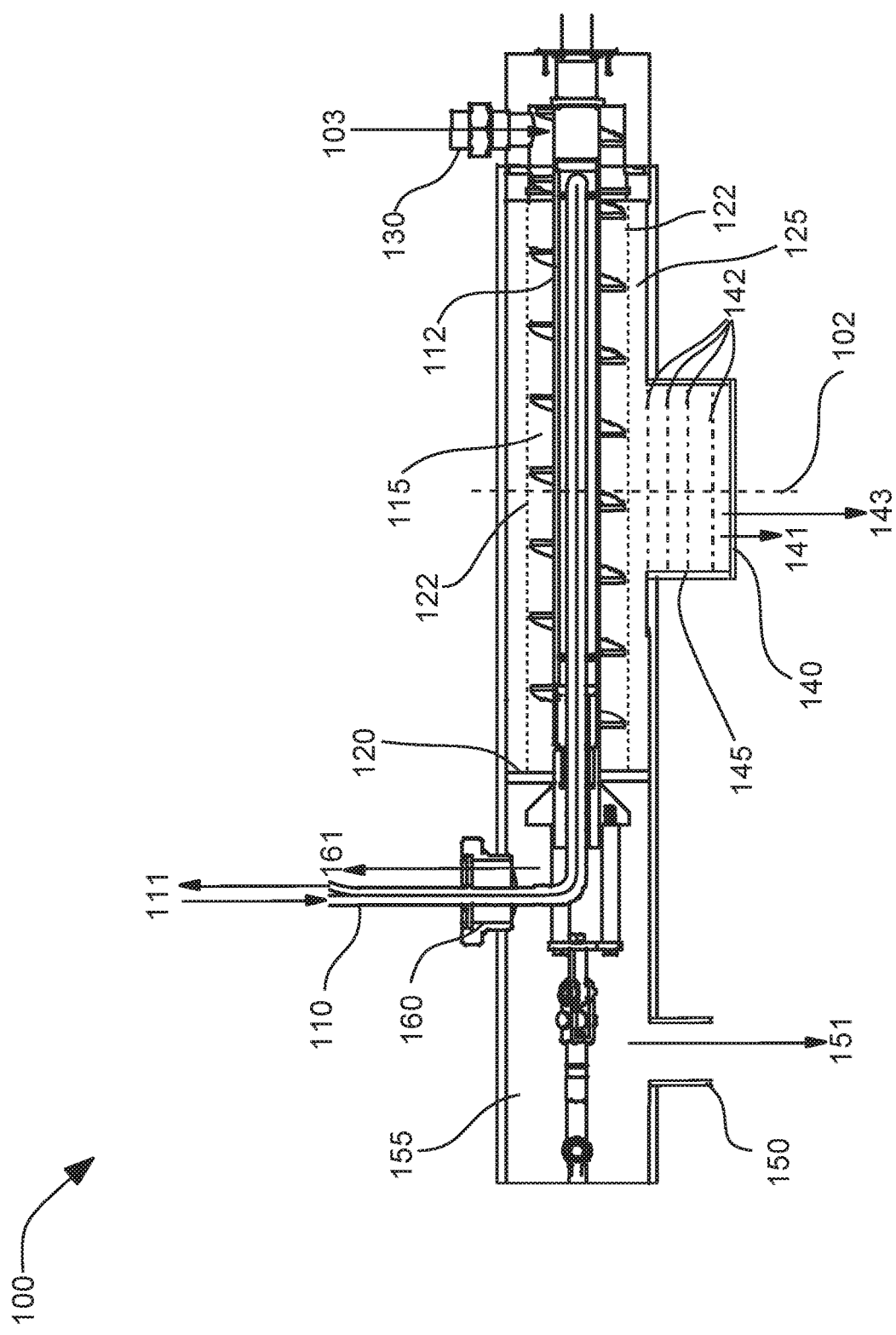
FIG. 1A is a cutaway top view of a screw auger filter press with a built-in gravity separator.

The following description recites various aspects and embodiments of the inventions disclosed herein. No particular embodiment is intended to define the scope of the invention. Rather the embodiments provide non-limiting examples of various compositions, and methods that are included within the scope of the claimed inventions. The description is to be read from the perspective of one of ordinary skill in the art. Therefore, information that is well known to the ordinarily skilled artisan is not necessarily included.

Definitions

The following terms and phrases have the meanings indicated below, unless otherwise provided herein. This disclosure may employ other terms and phrases not expressly defined herein. Such other terms and phrases shall have the meanings that they would possess within the context of this disclosure to those of ordinary skill in the art. In some instances, a term or phrase may be defined in the singular or plural. In such instances, it is understood that any term in the singular may include its plural counterpart and vice versa, unless expressly indicated to the contrary.

As used herein, the singular forms "a," "an," and "the" include plural referents unless the context clearly dictates otherwise. For example, reference to "a substituent" encompasses a single substituent as well as two or more substituents, and the like.

As used herein, "for example," "for instance," "such as," or "including" are meant to introduce examples that further clarify more general subject matter. Unless otherwise expressly indicated, such examples are provided only as an aid for understanding embodiments illustrated in the present disclosure, and are not meant to be limiting in any fashion. Nor do these phrases indicate any kind of preference for the disclosed embodiment.

As used herein, "filter medium" refers to any porous material through which a first material of a process stream may pass while a second material of the process stream may not pass, at least not in any significant quantities. For example, the first material may be a liquid while the second may be a solid.

As used herein, "filter separator" refers to any separation unit that uses a filter medium and has a settling chamber in which the separated liquids can gravity separate.

As used herein, "cryogenic" is intended to refer to temperatures below about −58° F. (−50° C.).

As used herein, "heating element" refers to any source of heat. Examples may include, but are not limited to, heat exchangers and electrical resistance heaters.

As used herein, "oxides" refers to any combination of sulfur oxides, nitrogen oxides, and ozone. Examples include, but are not limited to $NO_2$, $NO_3$, $SO_2$, $SO_3$, and $O_3$ As used herein, "quiescent settling chamber" refers to any chamber wherein flow is slowed enough that turbulent flow ceases and gravity separation of liquids can occur.

As used herein, "melter separator" refers to any chamber or combination of chambers comprising a heating element and a settling chamber where gravity-separation may occur.

FIG. 1A shows a cutaway top view 100 of a screw auger filter press with a built-in gravity separator that may be used with the methods herein. A feed stream 103 enters through a feed stream port 130 into a chamber 115. In this embodiment, the feed stream 103 is a mixture of solids and liquids. The solids consist of sulfur oxides and carbon dioxide. The liquids consist of nitrogen oxides and isobutene. An auger 112 is heated by flowing heating fluid 111 through tubing 110. The auger 112 forces the flow of the feed stream 103 through the chamber 115, pushing the concentrated solids through a restricted port 120 into a melter 155. Heating the auger 112 also melts the sulfur oxides out of the feed stream 103. A first portion of the liquids in the chamber 115 pass through the filter medium 122 into chamber 125. This first portion of liquids then passes into a settling chamber 145. The settling chamber 145 has flow-slowing screens 142. The liquids gravity-separate and exit through weirs 140 and 144. The solid carbon dioxide is melted in melter 155. The remaining concentrated flue particles 161 exit through lower port 160 and the significant majority of the liquids 151 exit upper port 150.

Figure 1B:
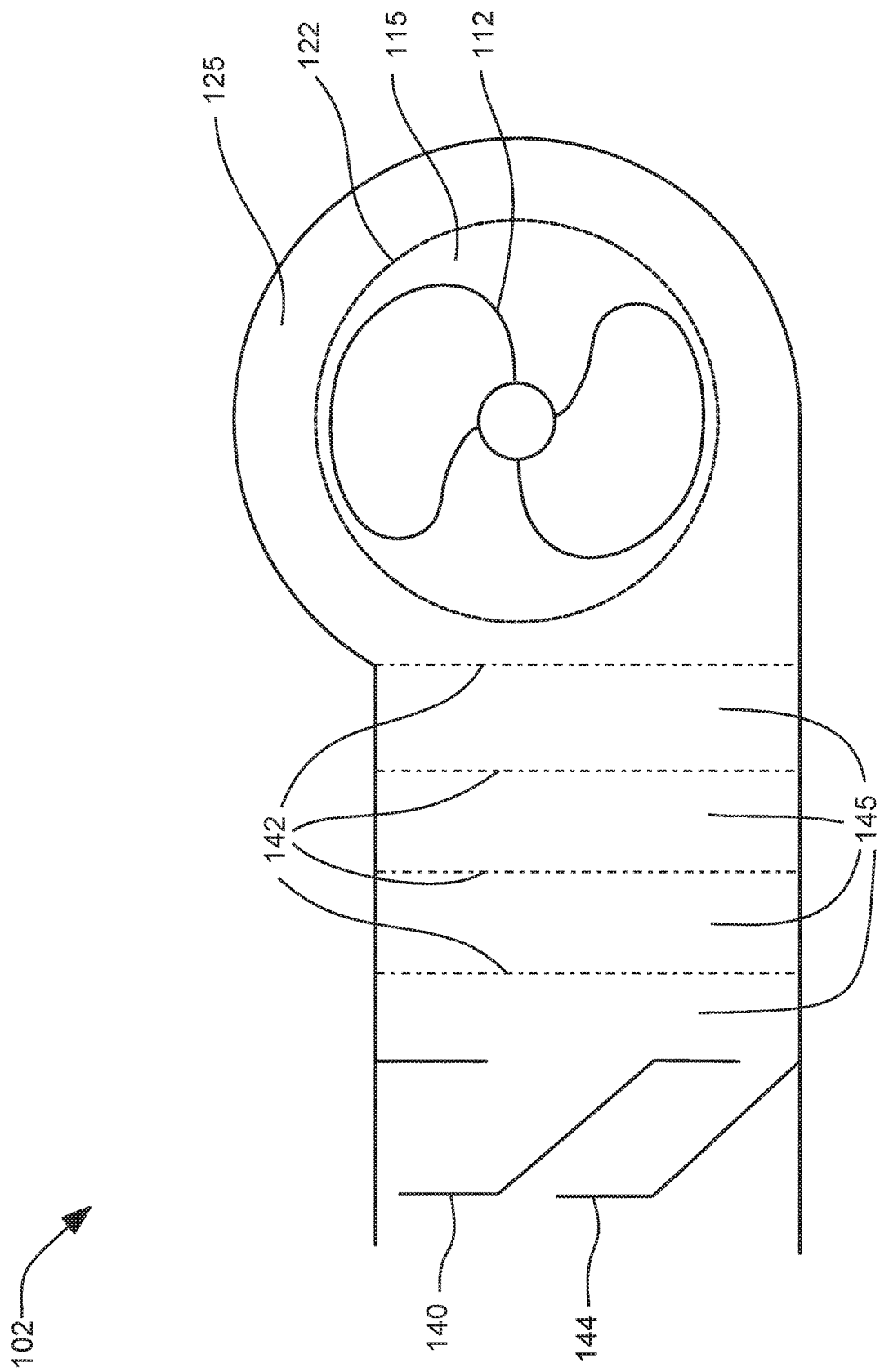
FIG. 1B is a cutaway side view of FIG. 1A.

As auger 112 conveys material through chamber 115 into the page of FIG. 1B, liquid is filtered out of chamber 115 through filter medium 122 and into chamber 125. The liquid then enters settling chamber 145 with flow being limited by the settling screens 142. The liquid gravity-separates and the denser liquid 143 leaves out weir 144 the less dense liquid 141 exits weir 140.

Figure 2:
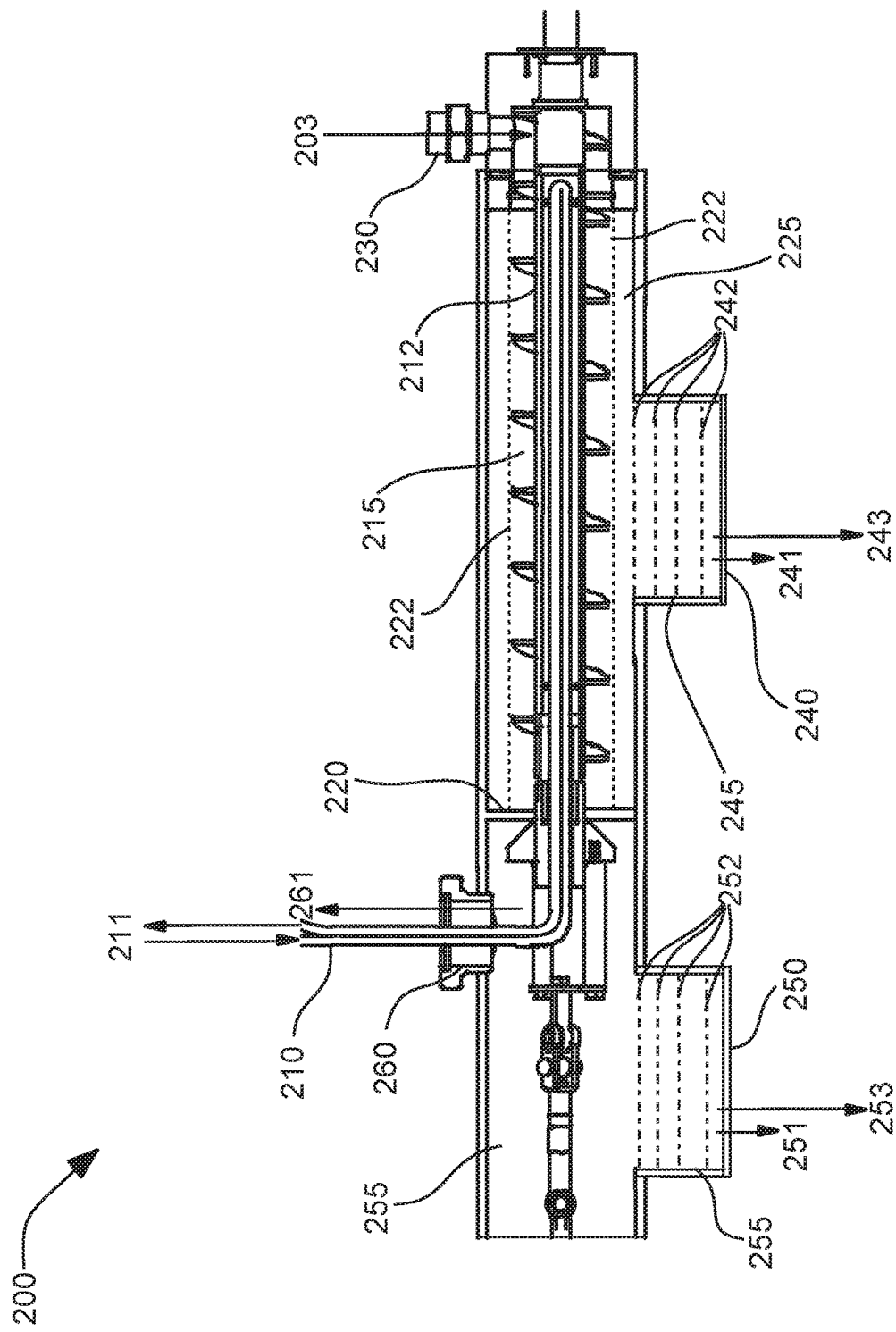
FIG. 2 is a cutaway side view of a melter separator unit with a quiescent settling chamber.

FIG. 2 shows a cut-away top view 200 of a screw auger filter press with a built-in gravity separator that may be used in the methods herein. A feed stream 203 enters through a feed stream port 230 into a chamber 215. In this embodiment, the feed stream 203 is a mixture of solids and liquids. The solids consist of carbon dioxide and oxides including nitrogen oxides, sulfur oxides, and ozone. The liquids consist of nitrogen oxide and the organic compound, propylene. An auger 212 is heated by flowing heating fluid 211 through tubing 210. The auger 212 forces the flow of the feed stream 203 through the chamber 215, pushing the concentrated solids through a restricted port 220 into a melter 255. Heating the auger 212 also melts the nitrogen oxides of the feed stream 203. A first portion of the liquids in the chamber 215 pass through the filter medium 222 into chamber 225. The first portion of the liquids then pass into a quiescent settling chamber 245. Quiescent settling chamber 245 has flow-slowing screens 242. The liquids gravity-separate and exit through weirs 240, with denser liquids leaving in stream 241 and the less dense liquids leave in stream 243. The solid carbon dioxide is melted in melter 255. A significant portion of the liquids then pass into quiescent settling chamber 255. Quiescent settling chamber 255 has flow-slowing screens 252. The liquids gravity-separate and exit through weirs 250, with denser liquids leaving in stream 251 and the less dense liquids leave in stream 253. The remaining concentrated flue particulates stream 261 exits through lower port 260. In some embodiments, the quiescent region could have a funnel-type geometry at the bottom to concentrate the oxides further.

Figure 3:
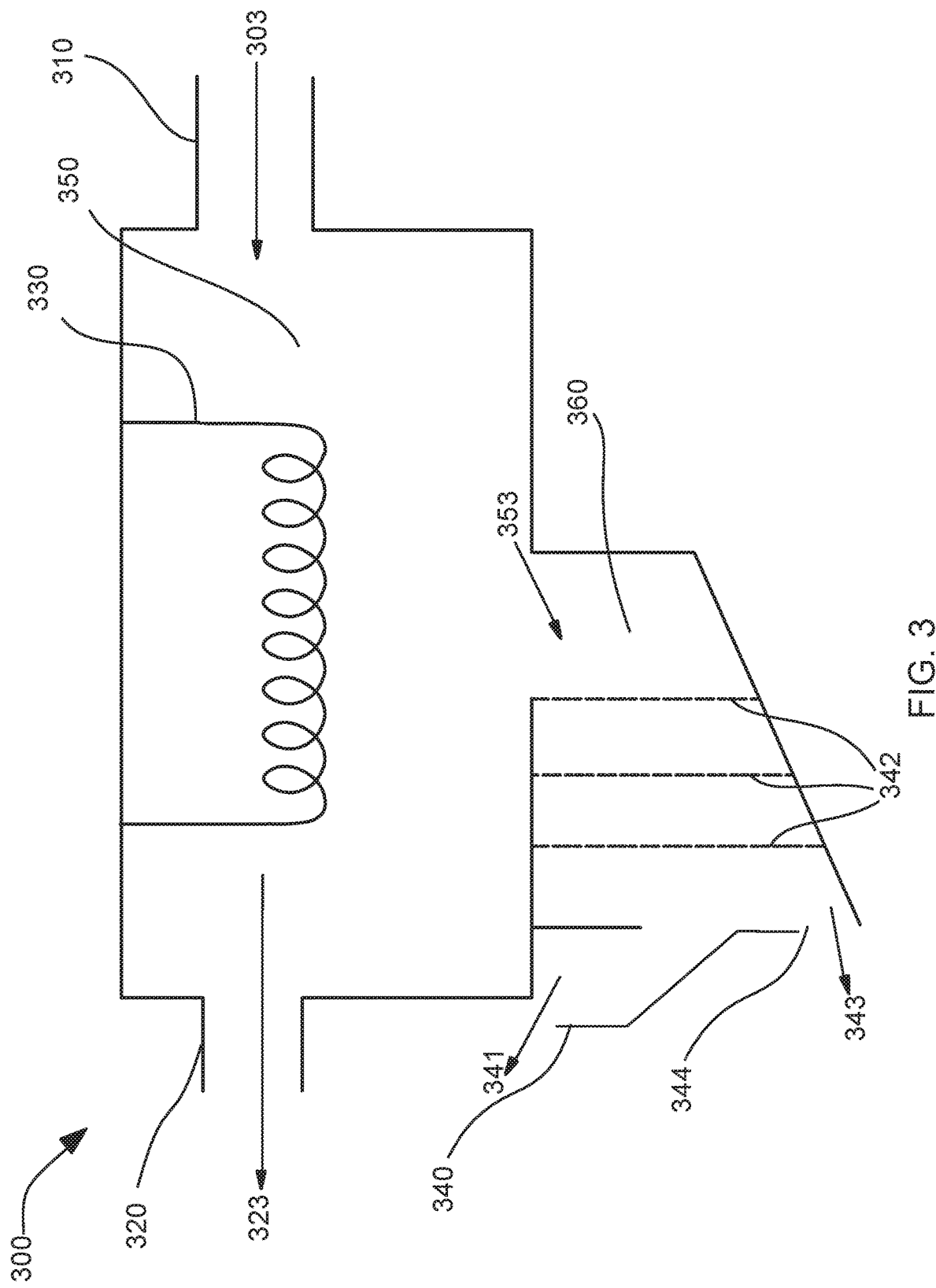
FIG. 3 is a cutaway top view of a screw auger filter press with two built-in gravity separators.

FIG. 3 is a cut-away side view 300 of a combined melter and settling chamber that may be used in the methods herein. Chamber 350 may be used in place of melter 255 in FIG. 2. Feed stream 303 enters melting chamber 350 through port 310. Feed stream 303 is composed of a liquid organic compound, a liquid nitrogen oxide, a solid sulfur oxide, a solid carbon dioxide, and flue particulates, which is composed of a mixture of solids and liquids. The sulfur oxides and a portion of the carbon dioxide solids are melted by heat provided by heating element 330. A portion of the carbon dioxide and the liquid organic compound exit port 320 as product stream 323. A portion of the carbon dioxide from product stream 323 may be recycled back into stream 303 before port 310. Solids and denser liquids 353 flow into quiescent settling chamber 360. The settling screens 342 help prevent excessive flow and allow the liquids gravity separate. The densest liquids and the solids exit out port 344 as product stream 343 and the less dense liquids exit weir 340 as product stream 341.

In some embodiments, the feed stream includes the carbon dioxide and the oxides as solids, liquids or a combination of solids and liquids. The method may also include the separator further comprising a heating element. The heating element allows for selective melting of the various components of the stream, allowing for staged separations. Solid-liquid phase separation techniques may be used to separate what would otherwise be two miscible liquids from each other.

The separator of the method may further comprise a filter medium. This would allow for the above-mentioned separation. The method may also include an auger in the separator, while a portion of the carbon dioxide and the oxides are solids. The auger may be heated to melt a portion of the oxides that are the solids to form a liquid oxides stream. The auger can be used to control solids flow through the separation unit. A portion of the liquid oxides stream may be separated from the solids and the organic phase by the filter medium. The inorganic phase may further settle into a quiescent settling chamber and may be decanted out of the separator. The method may also include separating the nitrogen oxide in the filter portion of the separator and the sulfur oxide in the welter of a filter separator. The method may include the feed stream further comprising compounds selected from a group consisting of water, ammonia, hydrogen sulfide, mercury, soot, dust, minerals, microbes, precipitated salts, precious metals, base metals, particulates, and combinations thereof.

In some embodiments, solid particles are separated from the feed stream, as they may interfere with the separation by gravity in the unit. These solid particles may be dust, sand, grit, coffee stirrers pennies, wrappers, ear plugs and other debris.

In some embodiments, the organic compounds consist of alcohols, ethers, hydrocarbons, or a combination thereof. In some embodiments, the hydrocarbons consist of 1,1,3-trimethylcyclopentane, 1,4-pentadiene, 1,5-hexadiene, 1-butene, 1-methyl-1-ethylcyclopentane, 1-pentene, 2,3,3,3-tetrafluoropropene, 2,3-dimethyl-1-butene, 2-chloro-1,1,1,2-tetrafluoroethane, 2-methylpentane, 3-methyl-1,4-pentadiene, 3-methyl-1-butene, 3-methyl-1-pentene, 3-methylpentane, 4-methyl-1-hexene, 4-methyl-1-pentene, 4-methylcyclopentene, 4-methyl-trans-2-pentene, bromochlorodifluoromethane, bromodifluoromethane, bromotrifluoroethylene, chlorotrifluoroethylene, cis 2-hexene, cis-1,3-pentadiene, cis-2-hexene, cis-2-pentene, dichlorodifluoromethane, difluoromethyl ether, trifluoromethyl ether, dimethyl ether, ethyl fluoride, ethyl mercaptan, hexafluoropropylene, isobutane, isobutene, isobutyl mercaptan, isopentane, isoprene, methyl isopropyl ether, methylcyclohexane, methylcyclopentane, methylcyclopropane, n,n-diethylmethylamine, octafluoropropane, pentafluoroethyl trifluorovinyl ether, propane, sec-butyl mercaptan, trans-2-pentene, trifluoromethyl trifluorovinyl ether, vinyl chloride, bromotrifluoromethane, chlorodifluoromethane, dimethyl silane, ketene, methyl silane, perchloryl fluoride, propylene, vinyl fluoride, or a combination thereof.

In some embodiments, the feed stream is in liquid phases and the liquids are separated out by means of a quiescent chamber and decanting.

In some embodiments, the first portion of the carbon dioxide is separated from the organic phase after it leaves the separator followed by recycling the carbon dioxide back into the separator. This could be a pressure control method allowing for a boost in efficiency.

In some embodiments, the separator operates at cryogenic temperatures allowing the system to operate at relatively low pressures as the oxides and ozone processed require either high pressures at moderate temperatures or cryogenic temperatures for relatively lower pressures.

The invention has been described with reference to various specific and preferred embodiments and techniques. Nevertheless, it is understood that many variations and modifications may be made while remaining within the spirit and scope of the invention.

What is claimed is:

1. A method for separating compounds comprising the steps of:
    passing a feed stream into a chamber, the feed stream including a feed stream liquid and solid oxides, the solid oxides comprising carbon dioxide and sulfur oxides;
    heating and melting the solid sulfur oxides in the chamber so that liquid sulfur oxides are formed;
    passing the feed stream liquid and the liquid sulfur oxides through a filter medium to filter the feed stream liquid and liquid sulfur oxides from the solid oxides of the feed stream, resulting in a filtered liquid;
    passing the filtered liquid into a settling chamber containing flow-slowing screens; and
    gravity-separating the filtered liquid in the settling chamber, wherein the filtered liquid separates into a denser liquid and a less dense liquid.

2. The method of claim 1, wherein the feed stream liquid comprises liquid oxides.

3. The method of claim 1, wherein the feed stream further comprises ozone.

4. The method of claim 1, further comprising moving the feed stream through a portion of the chamber using an auger.

5. The method of claim 4, further comprising heating the auger to heat and melt the solid sulfur oxides.

6. The method of claim 5, wherein the filter medium is positioned around the auger.

7. The method of claim 1, wherein the gravity-separating of the filtered liquid comprises decanting.

8. The method of claim 1, wherein the feed stream further comprises compounds selected from a group consisting of water, ammonia, hydrogen sulfide, mercury, soot, dust, minerals, microbes, precipitated salts, precious metals, base metals, particulates, and combinations thereof.

9. The method of claim 1, further comprising operating at cryogenic temperatures.

* * * * *